United States Patent [19]

Mennen

[11] 3,954,564

[45] May 4, 1976

[54] **INSTRUMENT FOR THE DETECTION OF *NEISSERIA GONORRHOEAE* AND THE LIKE**

[76] Inventor: Frederick C. Mennen, 506 Clay St., La Porte, Ind. 46350

[22] Filed: Mar. 25, 1975

[21] Appl. No.: 561,707

Related U.S. Application Data

[63] Continuation-in-part of Ser. No. 193,739, Oct. 29, 1971, Pat. No. 3,876,503.

[52] U.S. Cl. .............................................. 195/127
[51] Int. Cl.² ........................................ C12K 1/00
[58] Field of Search .............. 195/127, 139, 103.5 R

[56] References Cited
UNITED STATES PATENTS

| | | | |
|---|---|---|---|
| 3,446,596 | 5/1969 | Salivar et al. | 23/253 TP |
| 3,890,954 | 6/1975 | Greenspan | 195/139 |

*Primary Examiner*—Alvin E. Tanenholtz
*Attorney, Agent, or Firm*—Abraham A. Saffitz

[57] ABSTRACT

A disposable instrument for *Neisseria gonorrhoeae* making use of an oxidase reagent impregnated in a dry pledget that is activated by being wetted at the time of the test comprising a flexible transparent tube surrounding a frangible ampul containing a wetting fluid to activate the reagent and the pledget, both held in a reaction chamber within the tube by a restriction in the tube and a swab held separated from the pledget by the restriction until a test specimen has been collected thereon. After the specimen has been collected, the swab is reinserted in the tube, forced past the restriction and into contact with the pledget. The frangible ampul is broken by squeezing the flexible tube, and the instrument may be sealed with a cap as the test proceeds. Within a time period of from 30 to 120 seconds, the test is completed and the results may be noted by observing whether or not there has been a change of color of the pledget, which can be observed through the transparent wall of the tube, whereupon the sealed instrument may then be safely disposed of.

1 Claim, 5 Drawing Figures

U.S. Patent    May 4, 1976    3,954,564
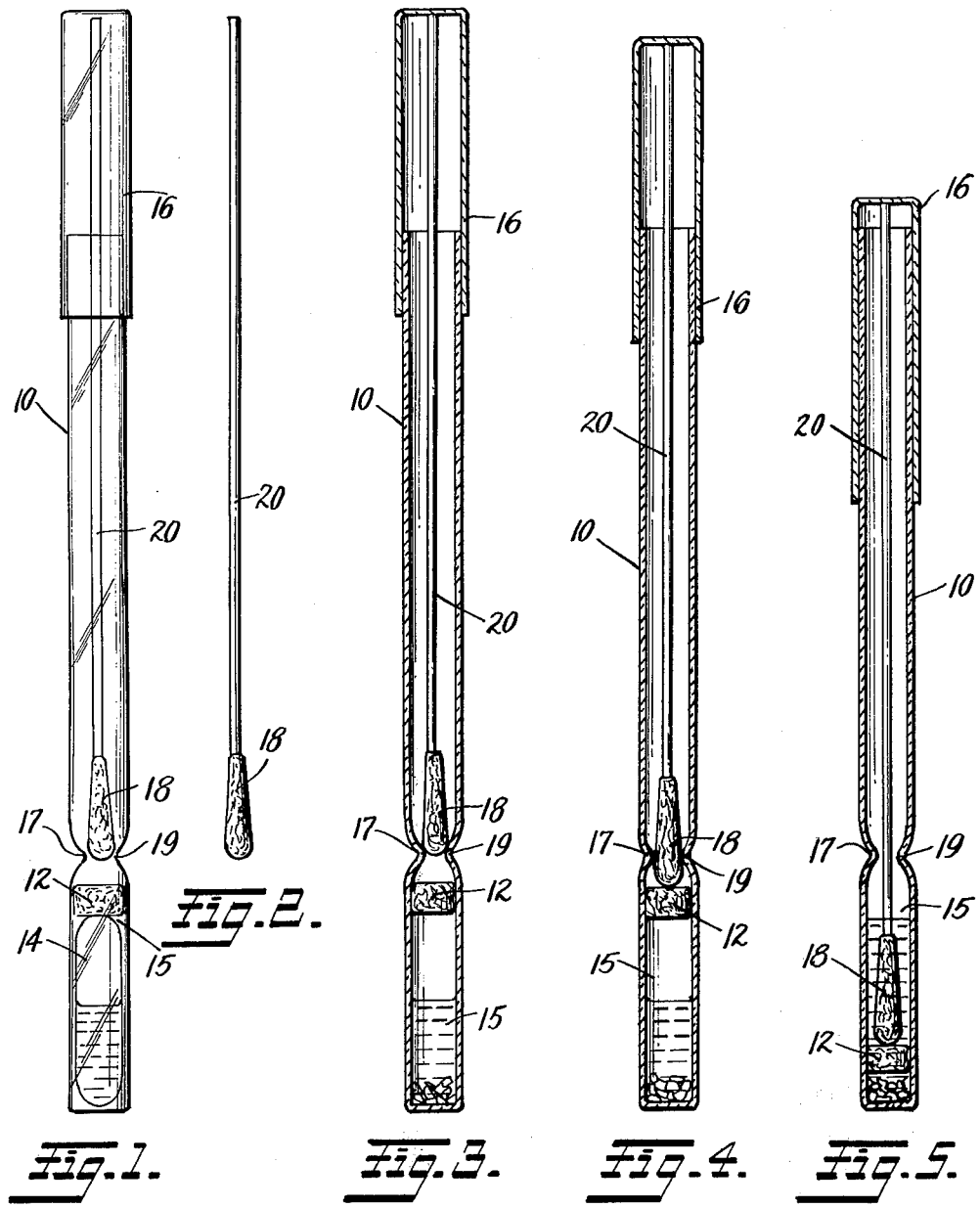

INSTRUMENT FOR THE DETECTION OF NEISSERIA GONORRHOEAE AND THE LIKE

CROSS-REFERENCE TO RELATED APPLICATIONS

This application is a continuation-in-part of my copending application, Ser. No. 193,739, filed Oct. 29, 1971, entitled METHOD AND INSTRUMENT FOR THE DETECTION OF NEISSERIA GONORRHEAE WITHOUT CULTURE, now U.S. Pat. No. 3,876,503, issued Apr. 8, 1975. This parent application is specifically incorporated by reference herein.

Copending application, Ser. No. 537,593, filed Dec. 30, 1974 as a divisional under 37 CFR 1.60 of Ser. No. 193,739, entitled METHOD AND INSTRUMENT FOR THE DETECTION OF NEISSERIA GONORRHEAE WITHOUT CULTURE.

Copending application, Ser. No. 563,300 filed on even date herewith, Mar. 28, 1975 entitled APPARATUS ESPECIALLY USEFUL FOR DETECTION OF NEISSERIA GONORRHOEAE AND THE LIKE IN FEMALES.

BACKGROUND OF THE INVENTION

1. Field of the Invention
a. Present Status of the Problem

It is common knowledge that this country and most of the world is undergoing a verneral disease epidemic. In the United States along the disease has reached pandemic proportions. It is estimated that only one-fifth of the cases are reported and only one-third reach the attention of physicians and Public Health authorities in order to receive treatment. The availability of a simple, rapid and inexpensive test would aid in recognition and control of this disease.

The usual clinical evidence of a gonorrheae infection in the male is a purulent discharge form the meatus and urethra of the penis. As routine procedure it is necessary to make a differential diagnosis of the nature of the discharge before antibiotics can be prescribed. As a rule the first test is to determine if the urethritis is gonococcal or non-specific in nature.

2. Summary of the Prior Art

While some prior art, U.S. Pat. No. 3,450,129, Avery et al, makes use of frangible ampuls for carrying reagents, the use of that method is directed specifically to transporting a living bacterial specimen to a laboratory for culture and using their apparatus and method for the purpose of preserving the viability of the bacteria until they can be cultured, the purpose is to provide a concentration of micro-organism, whereas this invention is a diagnostic one-use disposable test system and does not require culture. It is a direct test on the few organisms present in the urethral tract picked up on a sterile swab inserted therein. Diagnosis is made at the time of collection of the specimen.

OBJECTS OF THE INVENTION

An object of this invention is therefore to probide a disposable device system which will operate directly on the patient and give the clinician or physician a simple, directly reading diagnostic tool which is time saving, inexpensive and reliable.

A further object of the invention is to provide an instrument which tests and kills the organism by reason of the toxicity of the testing reagent yet is disposed of easily without bringing into contact with the hands of the clinician or physician with the discharge of the patient.

Still a further object of the invention is to provide a capped easily disposable one-use diagnostic instrument for testing Neisseria gonorrhoeae.

SUMMARY OF THE INVENTION

The invention disclosed herein provides an improved disposable testing device for use with the procedure disclosed and claimed in the parent application Ser. No. 193,739, filed Oct. 29, 1971, now U.S. Pat. No. 3,876,503, issued Apr. 8, 1975 and includes a method for making use of this improved device after which it may be disposed of in a hygenic manner.

The principal object of this invention is to provide a diagnostic apparatus that may be conveniently used to detect Neisseria gonorrhoeae without making use of a culture or the classical gram-staining method, both of which are concuming and expensive to perform and require trained technicians and laboratory equipment.

The present invention involves the use of a reagent such as an oxidase testing reagent as disclosed in the application Ser. No. 193,739. In the following the teaching of that invention, a pledget or carrier of any suitable material such as dacron fiber, cotton fiber, or other porous material is impregnated or saturated with one of the disclosed reagents and then dried. It remains in the dry state until it is activated by a wetting agent.

The pledget is the principal compenent of the diagnostic system, as it contains the reactive chemical that is capable of identifying the gonococcus. In the dry state the oxidase reagent impregnated in the pledget will remain stable and is capable of long shelf life. The second part of the system is the wetting agent which is separated from the pledget by virtue of being contained in a frangible ampul. When the frangible ampul is crushed, the wetting agent contained therein is released, activating the reagent in the pledget. The pledget after, thus, being sensitized is brought into contact with the specimen on the tip of the collecting swab, reacting with the gonococci present, causing the specimen located on the swab to take on a characteristic color depending on the choice of reagent used. The pledget being white or nearly colorless in appearance does not cause any confusion during the test, because ti does not react colorimetrically. The color change takes place on the specimen collected on the swab. The reaction time to indicate a positive specimen usually falls within the range of from 30 to 120 seconds.

As a screening test for gonorrheae in public V-D clinics, hospitals, physicians' offices and the Armed Forces, the present device serves as an inexpensive and accurate differential diagnostic aid to assist the physician or clinic in the choice for drug treatment. The need for a simple and in expensive diagnostic system that can function in the field, independent of bacteriological and microscopic tests, is therefore well established. A method for such a test and an instrument for performing such a test is disclosed in my application Ser. No. 193,739, filed Oct. 29, 1971, entitled Method and Instrument for the Detection of Neisseria Gonorrheae without Culture, and in the 37 LFR 1.60 Divisional Application Ser. No. 537,593, filed Dec. 30, 1974.

BRIEF DESCRIPTION OF THE DRAWINGS

In order to illustrate more fully the manner in which this improved apparatus is used and its structure, reference is made to the drawings wherein:

FIG. 1 is an elevational view of the preferred form of my disposable diagnostic reagent system;

FIG. 2 is an elevational view of the swab removed from its protective tube and having a specimen thereon;

FIG. 3 is a vertical sectional view showing the swab replaced in the system with the wetting agent ampul being broken to expose the wetting agent;

FIG. 4 is a vertical sectional view, similar to FIG. 3, illustrating the intermediate position of the swab as it is being inserted into the reaction chamber; and FIG. 5 is a vertical sectional view showing the swab pushed downwardly into the reaction chamber into contact with the pledget that has been activated by the wetting agent.

DESCRIPTION OF THE PREFERRED EMBODIMENT(S)

Referring more specifically to the drawing, which represents one type of instrument capable of performing my test procedure, numeral 10 indicates a tube of transparent, flexible plastic, into which is inserted a pledget 12 of cotton impregnated or saturated with the oxidase reagent and dried. The pledget is seated on a frangible glass ampul 14 disposed in the closed end of the tube as shown in FIG. 1, which forms a reaction chamber 15.

Above the pledget, the tube is pinched in to form a restriction in the internal passageway in the tube, the restriction being indicated as inwardly facing shoulders 17 and 19. A sterile swab 18 with a plastic handle 20 to be used in obtaining a specimen to be analyzed is inserted in the tube, the swab resting on shoulders 17 and 19 to be held out of contact with the impregnated pledget. A cap 16 is fitted to the tube to complete the apparatus.

It should be noted that while the wall structure of the plastic tube is flexible, it has sufficient rigidity normally to maintain a generally cylindrical shape whereby to form a suitable container for the apparatus, and when it is put to use to permit easy insertion of the swab after a specimen to be tested has been taken. The ampul contains a suitable wetting agent, as described in my earlier application, and is sufficiently frangible that it can readily be broken when the sides of the flexible tube are pressed inwardly between the thumb and forefinger, whereupon the ampul shatters to release the fluid contained therein into the reaction chamber 15 as shown in FIGS. 3 and 4.

When a diagnostic test for gonorrheae is to be made, the package is opened, cap 16 is removed, the sterile swab is removed from tube 10, and a specimen is collected on the tip of the swab. The swab is reinserted, tip first, into the plastic tube. The telescopic cap is then replaced. The flexible tube is then squeezed at the ampul portion, breaking same and releasing its contents. Simultaneously, the telescopic cap is pushed down, forcing the specimen containing swab past shoulders 17 and 19 into contact with the pledget. This action also forces the pledget down into the wetting agent, activating the system. The specimen on the swab turning purple within from 30 seconds to 2 minutes is a positive test for gonorrheae as explained in my application, Ser. No. 193,739. The use of this test, gives the physician or clinian a rapid and accurate diagnostic tool in the first step of his differential diagnosis.

The reaction proceeds within the enclosed apparatus with a minimum change of exposure of the test reagent or specimen being analyzed. Upon completion of the test, the sealed apparatus may be incinerated or otherwise disposed of in a sanitary manner.

It is possible that certain of the active reagents used in performing this test, might have an irritating effect if deposited on human mucous membrane, it should be noted therefore that the swab 18 is maintained out of contact with pledget 12 which contains the reagent, as long as it rests on shoulders 17 and 19 and ampul 14 remains intact. As long as the apparatus is properly handled prior to use such separation between the swab and the reagent on the pledget is maintained. When the test is in progress, however, and the swab with the specimen thereon is to be tested, the swab is easily forced past shoulders 17 and 19 by pushing down on cap 16 to drive the pledget into the wetting agent. The specimen is immediately in contact with the pledget and the chemicals with which it has been impregnated so that when the pledget is wetted the test reaction proceeds without interference.

One example of an apparatus here shown includes an ampul 14 filled with a physiological saline solution at a pH of 7. A cotton pledget 12 that had been impregnated with a 1% dip in N, N, N, ', N'-tetramethyl-p-phenylenediamine dihydrochloride solution and then dried, was positioned over the ampul at the closed end of the tube. Then the tube was passed through two heated jaws to deform its wall to form shoulders 17 and 19 to reduce the space on the inside of the tube between the shoulders to about 3/16 of an inch to create the means for holding swab 18 out of contact with the impregnated pledget for the purpose described above.

The operation of the structure above described has been set forth with the description of the cooperative parts and need not be elaborated. It should be evident, however, that the shoulders 17 and 19 serve the dual function of holding the swab and pledget apart before the test is started and after completion of the test, prevent a displacement of a possibly infected swab before it can be effectively destroyed.

The above description covers the preferred method and apparatus of this invention. It is possible that modifications thereof may occur to those skilled in the art that will fall within the scope of the following claims.

What I claim is:

1. A disposable instrument for use in the rapid detection of *Neisseria gonorrhoeae* without gram-staining and without culture comprising:

an elongated tube having transparent wall means;
said tube being closed at one end and open at the other end;
a replaceable cover means for said open end;
said tube and its cover containing a dry pledget that has previously been impregnated with an oxidase indicating reagent, a frangible ampul containing a wetting agent for activating said reagent, and a swab disposed at the end of a handle means that is approximately as long as said tube;
said ampul being disposed in said tube adjacent the closed end thereof;
said pledget being disposed between said ampul and the open end of said tube;
a restriction in said tube between the pledget and the open end thereof, said restriction defining a reaction chamber in said tube adjacent the closed end thereof;

the wall of said tube adjacent the reaction chamber being flexible; and, said restriction normally holding the swab out of contact with the pledget but permitting the swab to be inserted into the reaction chamber from the open end of the tube after a test specimen has been collected on the swab and thereafter serving to hold the swab in contact with the pledget, said restriction being provided so that after the ampul has been fractured by squeezing the flexible wall means of the tube against it to release the fluid contained therein, the reagent impregnated in the pledget becomes activated and the specimen on the swab can be placed in contact therewith and the cap can be replaced on the tube so the test can proceed and upon completion thereof the instrument can be disposed of as a sealed unit.

* * * * *